US012636490B2

(12) United States Patent
Maschino et al.

(10) Patent No.: US 12,636,490 B2
(45) Date of Patent: May 26, 2026

(54) IMPLANTABLE MEDICAL DEVICES AND METHODS OF USE

(71) Applicant: Medicool Technologies Inc., Rochester, MN (US)

(72) Inventors: Steve Maschino, Rochester, MN (US); Samuel J. Asirvatham, Rochester, MN (US); Jeffrey Rynbrandt, Traverse City, MI (US); Charles Ritrivi, Houston, TX (US); Paul A. Friedman, Rochester, MN (US); Richard Scott Sanders, San Juan Capistrano, CA (US)

(73) Assignee: Medicool Technologies Inc., Rochester, MN (US)

( * ) Notice: Subject to any disclaimer, the term of this patent is extended or adjusted under 35 U.S.C. 154(b) by 857 days.

(21) Appl. No.: 17/743,023

(22) Filed: May 12, 2022

(65) Prior Publication Data
US 2022/0362545 A1     Nov. 17, 2022

Related U.S. Application Data

(60) Provisional application No. 63/187,994, filed on May 13, 2021.

(51) Int. Cl.
| | |
|---|---|
| *A61N 1/05* | (2006.01) |
| *A61N 1/375* | (2006.01) |
| *A61N 1/378* | (2006.01) |
| *A61N 1/39* | (2006.01) |

(52) U.S. Cl.
CPC ......... *A61N 1/0563* (2013.01); *A61N 1/0573* (2013.01); *A61N 1/37518* (2017.08); *A61N*

*1/378* (2013.01); *A61N 1/3956* (2013.01); *A61N 2001/058* (2013.01)

(58) Field of Classification Search
CPC .............. A61N 1/0563; A61N 1/37518; A61N 2001/058; A61F 2007/0075
See application file for complete search history.

(56) References Cited

U.S. PATENT DOCUMENTS

| | | | | |
|---|---|---|---|---|
| 5,876,422 | A * | 3/1999 | van Groeningen .. | A61N 1/3622 607/9 |
| 6,595,989 | B1 * | 7/2003 | Schaer ............. | A61B 17/22004 606/41 |
| 2004/0167581 | A1 * | 8/2004 | Mower ................ | A61N 1/3622 607/17 |
| 2009/0012576 | A1 * | 1/2009 | Erbstoeszer ......... | A61N 1/3752 607/38 |
| 2009/0024194 | A1 * | 1/2009 | Arcot-Krishnamurthy ................ A61F 7/123 607/113 |

(Continued)

FOREIGN PATENT DOCUMENTS

| | | | | |
|---|---|---|---|---|
| CA | | 2959181 A1 * | 3/2016 | ......... A61B 17/3423 |

*Primary Examiner* — John R Downey
*Assistant Examiner* — Karmel J Webster
(74) *Attorney, Agent, or Firm* — Fish & Richardson P.C.

(57)     ABSTRACT

This document describes implantable medical devices and methods of using such devices. The implantable medical devices include a cardiac lead sized for insertion in a cardiac cavity, the cardiac lead having a distal end and a proximal end and a lead body extending therebetween, a heat exchange module disposed at the distal end of the lead body, the heat exchange module comprising an enclosure having a first surface and a second surface, and one or more temperature sensors located within the enclosure.

17 Claims, 5 Drawing Sheets

(56)            References Cited

U.S. PATENT DOCUMENTS

| | | | |
|---|---|---|---|
| 2009/0163927 A1 * | 6/2009 | Ransbury | A61M 39/0613 |
| | | | 606/129 |
| 2010/0305632 A1 * | 12/2010 | Maskara | A61N 1/3629 |
| | | | 607/3 |
| 2011/0251676 A1 * | 10/2011 | Sweeney | A61F 2/2436 |
| | | | 623/1.23 |
| 2015/0133952 A1 * | 5/2015 | Seifert | A61B 17/3415 |
| | | | 607/116 |
| 2016/0121102 A1 * | 5/2016 | Tockman | A61N 1/059 |
| | | | 607/129 |
| 2017/0265892 A1 * | 9/2017 | Winegar | A61B 17/4241 |
| 2018/0360652 A1 * | 12/2018 | Ritrivi | A61F 7/007 |

* cited by examiner

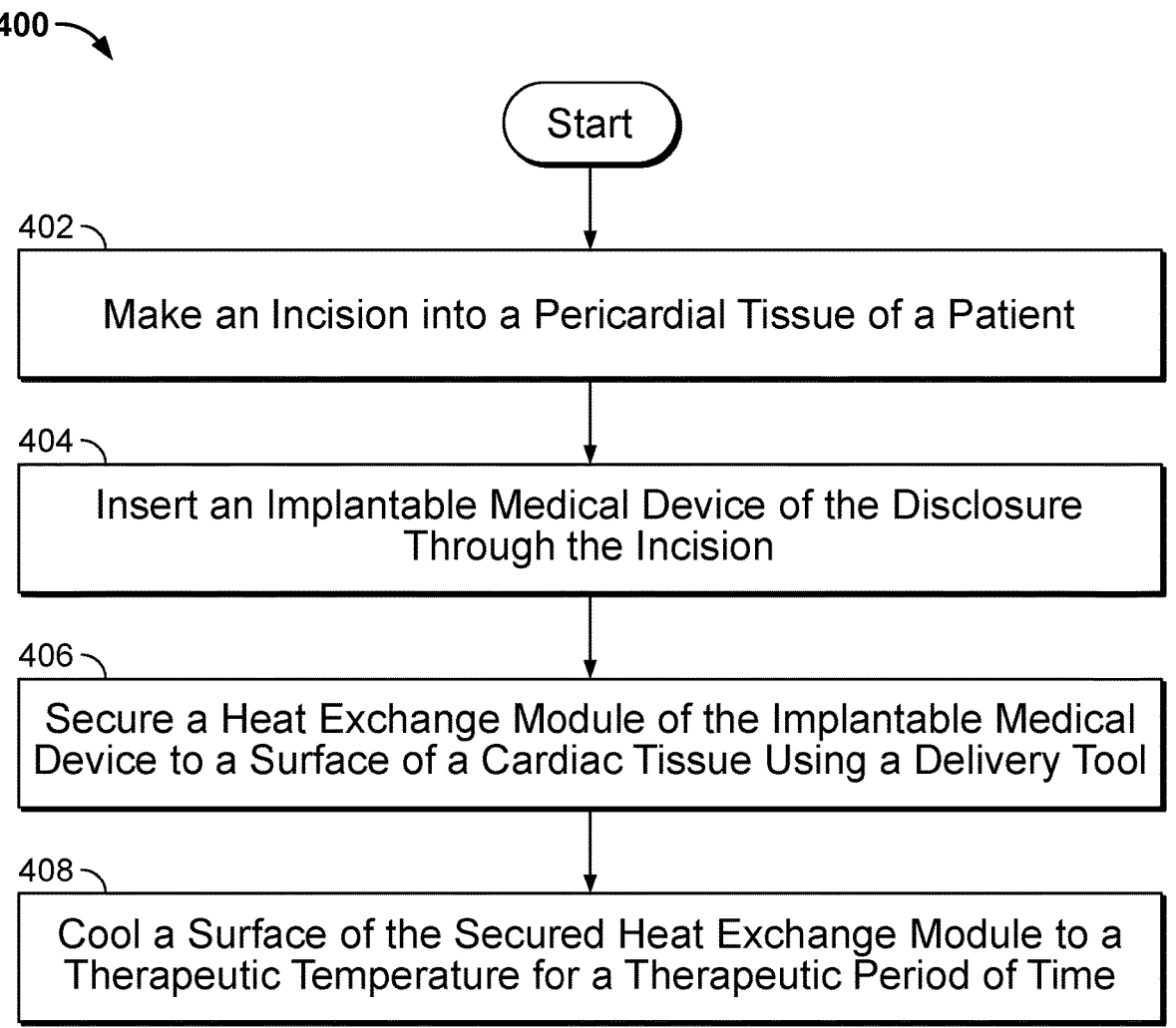

400

Start

402 — Make an Incision into a Pericardial Tissue of a Patient

404 — Insert an Implantable Medical Device of the Disclosure Through the Incision 406 — Secure a Heat Exchange Module of the Implantable Medical Device to a Surface of a Cardiac Tissue Using a Delivery Tool 408 — Cool a Surface of the Secured Heat Exchange Module to a Therapeutic Temperature for a Therapeutic Period of Time

FIG. 4

IMPLANTABLE MEDICAL DEVICES AND METHODS OF USE

CROSS-REFERENCE TO RELATED APPLICATIONS

This application claims priority to U.S. Provisional Application No. 63/187,994, filed on May 13, 2021, the contents of which are hereby incorporated by reference in its entirety.

BACKGROUND

1. Technical Field

This document relates to devices and related methods for delivering cooling therapy. For example, this document relates to implantable devices and related methods for the treatment of cardiac arrhythmias using temperature modulation.

2. Background Information

Cardiac arrhythmias occur when there is a change in the rate and/or rhythm of the heartbeat due to changes in the normal sequence of cardiac electrical impulses. Abnormalities of cardiac rate and/or rhythm are associated with substantial morbidity and economic costs. Different types of cardiac arrhythmias include atrial, bradycardia, conduction disorders, premature contraction, tachycardia, and ventricular fibrillation.

Among these conditions, atrial fibrillation is the most common arrhythmia encountered in clinical practice, affecting over 2.5 million Americans. Recently, cardiac arrhythmias have been reported in hospitalized coronavirus disease 2019 (COVID-19) patients, with one study reporting arrhythmias in 44% of individuals with severe illness. Studies have indicated the incidence of atrial fibrillation in the United States will increase to an estimated 12.1 million people in 2030.

Multiple prospective randomized trials have demonstrated the clinical benefit of implantable cardiac defibrillators (ICDs) in saving the lives of at-risk individuals, leading to their wide-spread adoption. A downside associated with ICD therapy, however, is the pain associated with defibrillation, whether shocks are delivered appropriately or inappropriately.

SUMMARY

In general, this disclosure describes implantable medical devices and related methods. Such implantable medical devices can be used to treat cardiac arrhythmias (e.g., atrial fibrillation) using temperature modulation.

In one aspect, this disclosure is directed to an implantable medical device including a cardiac lead sized for insertion in a cardiac cavity, the cardiac lead having a distal end and a proximal end and a lead body extending therebetween, a heat exchange module disposed at the distal end of the lead body, the heat exchange module including an enclosure having a first surface and a second surface, and one or more temperature sensors located within the enclosure.

In some embodiments, the implantable medical device further includes one or more pacing electrodes disposed at the distal end of the lead body. In some embodiments, the one or more pacing electrodes are disposed at a proximal and/or a distal end of the heat exchange module. In some embodiments, the implantable medical device further includes one or more sensing electrodes disposed on the lead body. In some embodiments, the implantable medical device further includes a delivery tool including a sheath having a proximal end and a distal end, the sheath defining an interior region configured to receive the lead body, and a case having a distal end sized for enclosing the heat exchange module and an elongate body configured to receive the sheath.

In some embodiments, the sheath has a tubular body, and the interior region of the sheath is a lumen. In some embodiments, the elongate body of the case is tubular. In some embodiments, the sheath has an open, semicylindrical body that defines a channel configured to receive the lead body. In some embodiments, the elongate body of the case comprises a flat surface configured to receive the sheath and a retention clasp configured to removably secure the sheath. In some embodiments, the case comprises a handle at a proximal end of the elongate body. In some embodiments, the sheath and case are composed of a flexible or malleable material.

In some embodiments, the implantable medical device further includes a suture sleeve disposed between the distal end and the proximal end of the cardiac lead, the suture sleeve configured to secure the implantable medical device adjacent to a cardiac tissue. In some embodiments, the suture sleeve is removably coupled and/or slidably coupled to the lead body. In some embodiments, the implantable medical device further includes one or more connectors at the proximal end of the cardiac lead, the one or more connectors configured to connect to a power supply.

In some embodiments, the one or more connectors comprise one or more lead terminal pins and one or more lead terminal rings. In some embodiments, the power supply is an implantable cardiac device. In some embodiments, the implantable cardiac device is an implantable cardioverter defibrillator (ICD), a pacemaker, or an external pulse generator. In some embodiments, the first surface of the heat exchange module is configured to be set to a first temperature that is less than a second temperature of the second surface of the heat exchange module. In some embodiments, the first temperature ranges from about 1 degree Celsius to about 37 degrees Celsius. In some embodiments, the second temperature ranges from about 37 degrees Celsius to about 50 degrees Celsius In some embodiments, the heat exchange module comprises a heat pump located within the enclosure, a heat sink located within the enclosure, the heat sink including a phase change material and a thermally conductive interface structure positioned between the heat pump and the phase change material. In some embodiments, the heat exchange module comprises one or more fixation filaments configured to secure the heat exchange module adjacent to a cardiac tissue, the one or more fixation filaments being loop-shaped. In some embodiments, the one or more fixation filaments are biased in an outward direction. In some embodiments, the heat exchange module is configured to be an indifferent electrode.

In another aspect, this disclosure is directed to a method of treating a cardiac arrythmia in a patient in need thereof, the method including making an incision into a pericardial tissue of the patient, inserting an implantable medical device through the incision, the implantable medical device including a cardiac lead sized for insertion in a cardiac cavity, the cardiac lead having a distal end and a proximal end and a lead body extending therebetween, a heat exchange module disposed at the distal end of the lead body, the heat exchange module including an enclosure having a first surface and a second surface, and one or more temperature sensors located within the enclosure, securing the heat exchange module to a surface of a cardiac tissue using a delivery tool including a sheath having a proximal end and a distal end, the sheath defining an interior region configured to receive the lead body, and a case having a distal end sized for enclosing the heat exchange module and an elongate body configured to receive the sheath, and cooling the first surface of the implantable medical device to a therapeutic temperature for a therapeutic period of time.

In some embodiments, the therapeutic temperature ranges from about 5 degree Celsius to about 15 degrees Celsius. In some embodiments, the therapeutic period of time ranges from about 5 seconds to about 60 seconds. In some embodiments, the first surface is configured to contact an epicardial tissue and the second surface is configured to contact a pericardial tissue when the implantable device is implanted. In some embodiments, the method further includes detecting a cardiac arrhythmia by using one or more sensing electrodes disposed on the lead body of the cardiac lead.

In some embodiments, the method further includes cooling the first surface of the implantable medical device upon detection of the cardiac arrhythmia. In some embodiments, the step of making the incision further comprises making an incision into an epicardial space of the patient. In some embodiments, the step of securing the heat exchange module further comprises attaching a suture sleeve to the cardiac tissue, wherein the suture sleeve is removably coupled and/or slidably coupled to the lead body.

Particular embodiments of the subject matter described in this document can be implemented to realize one or more of the following advantages. First, transient therapeutic tissue cooling therapy can be delivered using the devices and methods described herein. In some embodiments, the therapeutic tissue cooling can advantageously be delivered using a system that is fully implantable and self-contained. Accordingly, the patient receiving treatment can be fully ambulatory, and can experience a lifestyle that is relatively unhindered by the presence of the implantable therapeutic cooling device. In some embodiments, heart conditions such as arrhythmias and others can be treated using the devices and methods provided herein. In some embodiments, arrhythmias can be treated relatively painlessly. In some cases, such conditions can be treated in a minimally invasive fashion using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. In addition, the materials, methods and examples are illustrative only and not intended to be limiting.

The details of one or more embodiments of the invention are set forth in the accompanying drawings and the description below. Other aspects, features, and advantages of the invention will be apparent from the description, the drawings, and the claims.

DESCRIPTION OF DRAWINGS

FIG. 4 is a flowchart of an example method of treating a cardiac arrhythmia using the implantable medical devices of the disclosure.

Like reference numbers represent corresponding parts throughout.

DETAILED DESCRIPTION

The present disclosure describes implantable medical devices and related methods for delivering cooling therapy. For example, described herein are methods and devices for treating atrial and/or ventricular fibrillation by cooling the epicardium.

Implantable cardiac defibrillators (ICDs) can aid saving the lives of at-risk individuals. A downside associated with ICD therapy, however, is the pain associated with defibrillation, whether shocks are delivered appropriately or inappropriately.

In some embodiments, heart conditions, such as arrhythmias and others, can be treated using the devices and methods provided herein. In some embodiments described herein, arrhythmias can be treated by an implantable system for painlessly terminating arrhythmias. The devices and methods provided herein permit prompt termination of atrial fibrillation almost immediately after an episode begins (to prevent persistence) and is effective irrespective of patient age and comorbidities.

Figure 1:
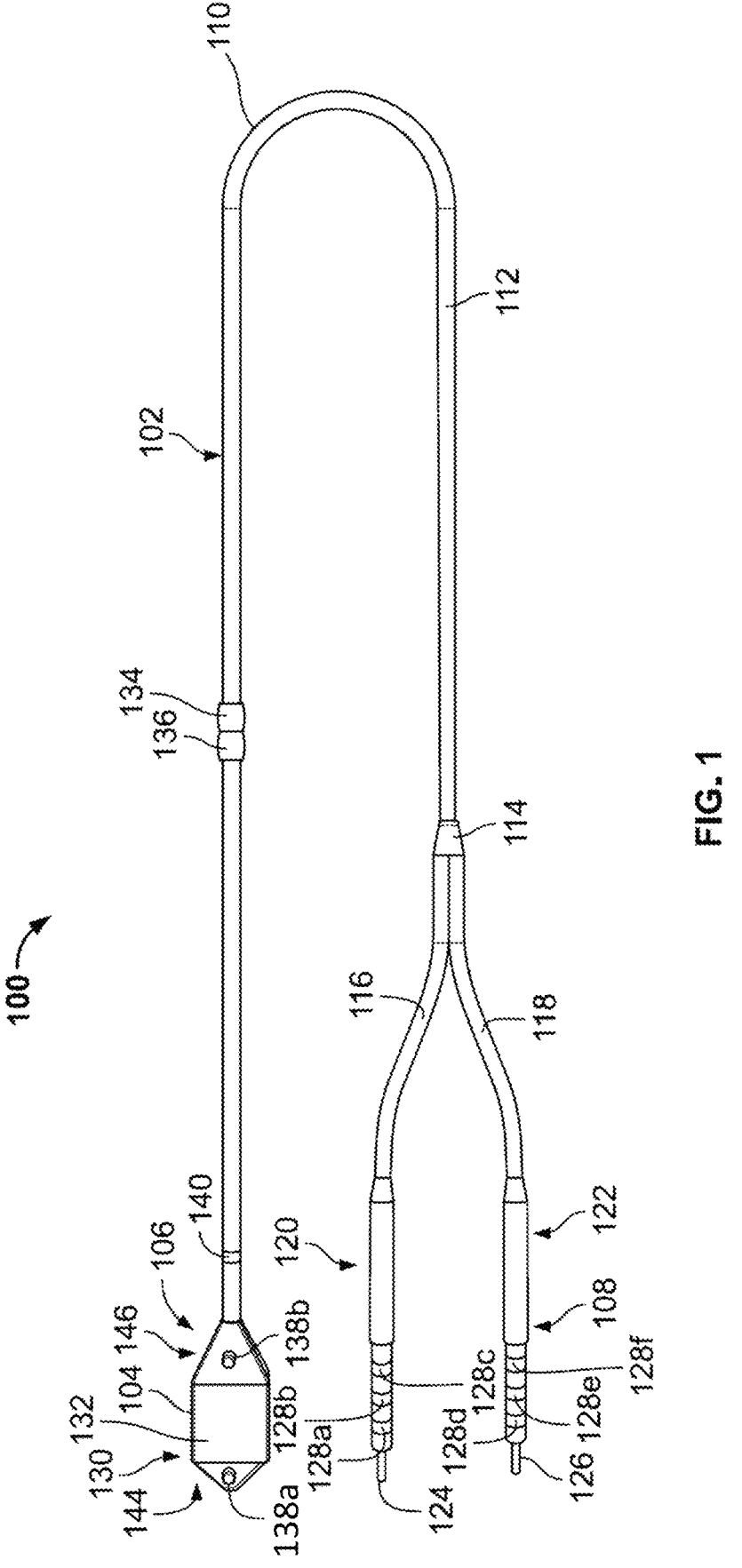
FIG. 1 is a top view of an implantable medical device that can be used to for the treatment of cardiac arrhythmias.

FIG. 1 illustrates an example implantable medical device 100 that can be used to deliver cooling therapy to a portion of a heart (e.g., a portion of a pericardium and/or epicardium) of a patient in need thereof. The implantable medical device 100 includes a cardiac lead 102 that is formed to be inserted in a cardiac cavity (e.g., an oblique sinus of the heart), and a heat exchange module 104 for cooling a portion of a surface of a heart. The cardiac lead 102 and the heat exchange module 104 together form a single component that is designed to be inserted and implanted into or on a heart of the patient. The implantable medical device 100 can be sterilized by methods known in the art (e.g., gamma irradiation, steam sterilization, chemical sterilization, and the like) prior to implantation. The single component can be provided in a sealed, sterile package that can be stored until a time of use.

The cardiac lead 102 includes a lead body 110 extending between a distal end 106 and a proximal end 108. The lead body 110 is a flexible elongate body. The lead body 110 includes an outer wall 112. The outer wall 112 defines an interior opening that is an elongate opening that extends along the length of the cardiac lead 102. The interior opening is sized to receive one or more electrical conductors (e.g., wires) that provide power to one or more components (e.g., sensors, heat pump, and/or heat sink) of the heat exchange module 104 and to one or more electrodes. The lead body 110 is a multi-lumen tube. In some embodiments, the outer wall 112 defines one or more interior openings. For example, the lead body 110 defines a central lumen that is concentric with an outer diameter of the lead body 110. In some embodiments, the central lumen may be offset from the center of the outer diameter. The structure of the cardiac lead 102 (e.g., including the interior opening), together with a material choice (e.g., a pliable biocompatible material), provides the cardiac lead 102 with a flexibility that allows the lead body 110 to be elastically (e.g., reversibly)

deformed (e.g., in bending). The flexibility of the cardiac lead 102 can advantageously facilitate positioning (e.g., by the surgeon) of the cardiac lead 102 during implantation. The interior opening of the lead body 110 and/or one or more electrical conductors can include an insulating material to support, insulate, and separate the electrical conductors to prevent current going through them from contacting other non-desired conductors (e.g., to prevent shorts and limit electrical leakage between the electrical conductors).

The lead body 110 of the cardiac lead 102 typically has a length of about 45 centimeters (cm) to about 75 cm (e.g., about 50 cm). The lead body 110 typically has an outer diameter of about 2.1 millimeters (mm) to about 3.1 mm (e.g., about 2.7 mm).

The lead body 110 is can be made of one or more materials typical of those used in the construction of implantable cardiac pacing and defibrillation leads. Example materials from which the lead body 110 may be made include silicone rubber, polyurethane, or silicone polyurethane copolymers. Example materials from which the insulating materials may be made include silicone rubber, polyurethane, polyether ether ketone (PEEK), polyurethane or polycarbonate.

The cardiac lead 102 includes a bifurcation 114 where the lead body 110 splits into a first portion 116 of the lead body 110 and a second portion 118 of the lead body 110. The bifurcation 114 is disposed along the lead body 110 in a location that is closer to the proximal end 108 than to the distal end 106 of the cardiac lead 102. In some embodiments, the bifurcation 114 can be positioned at a location that is about 75% distal from the distal end 106 of the cardiac lead 102. The first portion 116 of the lead body 110 includes a first lead connector 120, and the second portion 118 of the lead body 110 includes a second lead connector 122. The cardiac lead 102 can include one or more lead connectors disposed at the proximal end 108. The first and second lead connectors 120, 122 are configured to connect to a pulse generator. For example, the first and second lead connectors 120, 122 provide the electrical and mechanical connection between a pulse generator (e.g., a power source included in a pulse generator) and the proximal end 108 of the cardiac lead 102. The pulse generator can include a power source, a microprocessor, a memory storage, sensor circuitry (e.g., for sensing a temperature, heart rate, lead impedance, or the like), circuitry for delivering a voltage and/or a current output to stimulate the heart, and circuitry for delivering a voltage and/or current output to the Peltier device. The first and second lead connectors 120, 122 can provide an electrical and mechanical connection to one or more of any of the above-recited components of the pulse generator.

When inserted into the pulse generator, the one or more electrical conductors disposed within the first and second portions 116, 118 of the lead body 110 electrically couple the one or more components (e.g., sensors, heat pump, and/or heat sink) of the heat exchange module 104 and the one or more electrodes to the pulse generator. The pulse generator can be an implantable cardiac device. In some embodiments, the implantable cardiac device is an implantable cardioverter defibrillator (ICD) or a pacemaker. In other embodiments, this may be an external pulse generator. In some embodiments, the cardiac lead 102 can be configured to not pace the heart and/or to not sense an ECG. In this case, the cardiac lead 102 may only deliver power to the Peltier device and may only sense the temperature of the heat exchange module 104.

The one or more lead connectors include one or more lead terminal pins and one or more lead terminal rings. The first lead connector 120 includes a first terminal pin 124, and the second lead connector includes a second terminal pin 126. The first and second terminal pins 124, 126 provide the electrical connection between the pulse generator and the cardiac lead 102. The first lead connector 120 further includes a first lead terminal ring 128a, a second lead terminal ring 128b, and a third lead terminal ring 128c, which are coupled to the first portion 116 of the lead body 110. The second lead connector 122 further includes a fourth lead terminal ring 128d, a fifth lead terminal ring 128e, and a sixth lead terminal ring 128f, which are coupled to the second portion 118 of the lead body 110. Each lead terminal ring 128a, 128b, 128c, 128d, 128e, 128f provides an electrical connection between the cardiac lead 102 and a pulse generator.

In some embodiments, the first lead terminal ring 128a may be a return conductor that provides a path for the current in the system (e.g., in the implantable medical device 100) to flow back to the pulse generator. In some examples, the second lead terminal ring 128b and the third lead terminal ring 128c may be lead terminals to one or more temperature sensors. In some embodiments, the fourth lead terminal ring 128d may correspond to the lead terminal to a sensing electrode. In some examples, the fifth lead terminal ring 128e may correspond to the lead terminal to a reference sensing electrode. The sensing and reference or common sensing electrodes can be used to detect an electrical signal from a heart of the patient, as described in further detail below. The above-recited configurations are example configurations and each lead terminal ring may be connected to one or more different or same conductors. For example, in some embodiments, any one of the lead terminal rings can be configured to be or to connect to one or more conductors (e.g., a common/return conductor, one or more temperature sensors, a sensing electrode, a reference sensing electrode, a pacing conductor, a reference sensing electrode, or the like).

The electrical conductors connecting the first and second lead connectors 120,122 to the one or more components (e.g., sensors, heat pump, and/or heat sink) of the heat exchange module 104 and to the one or more electrodes, are typically made of one or more materials typical of those used in the construction of implantable cardiac pacing and defibrillation leads. Example materials from which the electrical conductors may be made include nickel cobalt chromium alloys such as MP35N®. Example materials from which the first and second lead terminal pins 124, 126 may be made include stainless steel alloys such as 316L, or Nickel Cobalt alloys such as MP35N®.

The lead body 110 includes a suture sleeve 134 disposed between the distal end 106 and the proximal end 108 of the cardiac lead 102. The suture sleeve 134 is configured to secure the implantable medical device 100 adjacent to a cardiac tissue. The suture sleeve 134 is removably coupled and/or slidably coupled to the lead body 110. The suture sleeve 134 is formed by a generally tubular portion defining a lumen that is configured to receive the cardiac lead 102. The suture sleeve 134 provides an aid for suturing and fixating the cardiac lead 102 at a desired position in the body (e.g., a portion of the heart, at the point of entry into a vein, or the like). Thus, the suture sleeve 134 is arranged to fixate the sleeve at a selected position along the lead body 110. The suture sleeve 134 includes a groove 136 bisecting the tubular portion of the suture sleeve 134 and configured to receive a suture. The groove 136 can be a circumferential groove or a circumferential recess that provides a guiding path onto which a suture can be tied and prevents the suture from sliding off the suture sleeve 134. In some embodiments, the lead body 110 includes a suture disk that can be used to seal an incision in the heart during implantation of the implantable medical device 100. The suture sleeve can couple with the suture disk to seal or close the incision in the heart.

The heat exchange module 104 is disposed at the distal end 106 of the lead body 110. The heat exchange module 104 is hermetically sealed and capable of cooling one of its surfaces. When implanted in the heart, the heat exchange module 104 can cool a portion of cardiac tissue (e.g. atrial tissue). In this manner, a cooling therapy can be delivered to a portion of a heart of a patient by cooling the cardiac tissue that is adjacent to, contacting, and/or in close proximity to a surface (e.g., the cold surface) of the heat exchange module 104. The cooling effect on the atrial tissue is believed to inhibit action potentials and allow the cardiac conduction system to return to sinus rhythm.

The heat exchange module 104 includes an enclosure 130 having a first surface 132 and a second surface. The heat exchange module 104 includes a heat pump (e.g., a Peltier element) located within the enclosure 130. The heat pump may include one or more thermoelectric cooling elements that use the Peltier effect to create a heat flux between the junction of two different types of materials. In contrast to the more commonly used vapor-compression refrigeration, Peltier cooling elements require no moving parts or circulating refrigerants, have a near infinite life, and can be made of a small size and flexible shape. These elements become thermally active when an electrical current is applied across them, with the temperature differential being a function of the current supplied into the system.

The first surface 132 of the heat exchange module 104 can be the cold surface, and the second surface of the heat exchange module 104 can be the hot surface, or vice versa. For example, the first surface 132 of the heat exchange module 104 is configured to be set to a first temperature that is less than a second temperature of the second surface of the heat exchange module. The first temperature can range from at least about 1 degree Celsius to about 37 degrees Celsius. (e.g., about 1 degree Celsius to about 5 degrees Celsius, about 5 degrees Celsius to about 10 degrees Celsius, about 10 degrees Celsius to about 15 degrees Celsius, about 15 degrees Celsius to about 20 degrees Celsius, 20 degrees Celsius to about 25 degrees Celsius, 25 degrees Celsius to about 30 degrees Celsius, or 30 degrees Celsius to about 37 degrees Celsius). The second temperature can range from at least about 37 degrees Celsius to about 50 degrees Celsius (e.g., about 37 degree Celsius to about 40 degrees Celsius, about 40 degrees Celsius to about 45 degrees Celsius, or about 45 degrees Celsius to about 50).

The hot surface and the cold surface are physically separated from each other and interconnected with each other by an array of alternating n-type and p-type semiconductors. The different types of semiconductors have complementary Peltier coefficients. Semiconductors are soldered between hot surface and cold surface, such that the semiconductors are electrically in series and thermally in parallel. As DC electric current flows through the heat pump (e.g., via electrical leads that are electrically connected to the heat pump), heat from cold surface is transferred to the hot surface, so that the cold surface gets cooler while hot surface gets hotter.

The heat exchange module 104 can further include one or more insulating materials. For example, the peripheral edges of the heat exchange module 104 are insulated from enclosure 130 by an insulative barrier. The insulative barrier can be just an electrical insulator, or just a thermal insulator, or both an electrical and a thermal insulator. Insulative barrier can be made of any suitable insulative material such as, but not confined to, Teflon®, phenolic cast resins, nylon, glass, and the like.

The heat exchange module 104 is hermetically sealed within enclosure 130 to protect the heat exchange module 104 (e.g., an inner chamber defined by enclosure 130) from body fluid ingress when implanted. Any biologically inert, highly heat conductive metal can be used to construct the enclosure 130 such that the heat exchange module 104 is isolated from body fluids. Such a biologically inert, highly conductive metal for the enclosure 130 can include, but is not limited to, titanium, titanium alloys, stainless steel, stainless steel alloys, 316 stainless steel, and the like, and combinations thereof. The enclosure 130 is also equipped with a means of allowing electrical leads (e.g., cardiac lead 102) to exit the enclosure 130 through glass feedthroughs, for example.

The heat exchange module 104 includes a heat sink located within the enclosure 130. The heat sink includes a phase change material and a thermally conductive interface structure positioned between the heat pump and the phase change material. A phase change material can be used to absorb the heat generated by the heat exchange module 104 and subsequently facilitate the gradual dissipation of the heat in a safe and effective manner. The phase change material can be a material with a melting temperature in the range of between about human body core temperature (37° C.) and about 50° C. (e.g., about 37° C. to about 41° C., about 41° C. to about 45° C., about 45° C. to about 50° C.). Phase change materials that are applicable due to their high specific heat, high heat of fusion and melting temperature in the range of about 37° C. and 50° C. include, but are not limited to, paraffins. In some embodiments, the phase change material has a very low thermal conductivity (e.g., about 0.2 watt per meter per degree Celsius ($W \cdot cm^{-1 \cdot °}C.^{-1}$)). Some desirable characteristics of the phase change material are low volume change with phase change, no toxicity, no corrosivity, and compatibility with the material of enclosure 130.

The heat exchange module 104 includes one or more fixation filaments 142 (refer to FIG. 2) configured to secure the heat exchange module 104 to a desired portion of a cardiac tissue (e.g., adjacent to a cardiac tissue). The heat exchange module 104 can be within the pericardial space of the heart by the deployment of the one or more fixation filaments 142 extending from the hot surface of the heat exchange module 104, which is located opposite the cold surface. The fixation filaments 142 are designed to apply gentle force to press the cold surface of the heat exchange module 104 against the target region of the pericardium, where the cooling therapy is applied. The fixation filaments 142 can be made of a corrosion resistant metal. Example materials from which the fixation filaments 142 may be made include nitinol or a nickel cobalt alloy such as MP35N®. The fixation filaments 142 may include biocompatible polymers for encapsulation of the metal structure and webbing, such as, but not limited to, polyethylene, polypropylene, nylon thermoplastics, or any combination thereof.

The one or more fixation filaments 142 are loop-shaped and biased in an outward direction so as to be biased to an open position but moveable rotationally inwardly when arms are closed. The one or more fixation filaments 142 are flexible and attached to the heat exchange module 104. When deployed, the one or more fixation filaments 142 provide compression against a target tissue (e.g., a tissue of the pericardial space), thereby pressing the cold surface of the heat exchange module 104 against the target tissue. The one or more fixation filaments 142 may be flexible enough to be rigidly attached to the heat exchange module 104 and resiliently deflectable inwardly, or they may be attached by a rotational coupling such as a pin or living hinge. The heat exchange module 104 can remain in place as an implant following deployment of the one or more fixation filaments 142.

The heat exchange module 104 can include one or more temperature sensors located within the enclosure 130. For example, the heat exchange module 104 includes a first temperature sensor and a second temperature sensor. The first and second temperature sensors are configured to measure a temperature of the first surface 132 and the second surface of the heat exchange module 104. The first and second temperature sensors are configured to measure a temperature of the cold and hot surfaces of the heat exchange module 104. As such, the first and second temperature sensors monitor the temperature of the heat exchange module 104. The first and second temperature sensors may monitor the temperature of a tissue surrounding the heat exchange module 104 once implanted. The first and second temperature sensors can provide feedback to a processor and/or controller (e.g., information regarding cooling efficacy, unwanted heating, and the like).

The cardiac lead 102 can include one or more pacing and/or electrocardiogram (ECG) sensing electrodes for monitoring of the heart and/or providing pacing therapy to cardiac tissue. The cardiac lead 102 includes a first pacing electrode 138a and a second pacing electrode 138b disposed at the distal end 106 of the lead body 110. The first and second pacing electrodes 138a, 138b can be configured for dual bipolar pacing of the atrium. In some embodiments, the first and second pacing electrodes 138a, 138b can be programmed to energized concurrently, or alternatively, and to pace each electrode independently or asynchronously relative to other electrode(s). The enclosure 130 or a sensing electrode (further described in detail below) on the heat exchange module 104 can be configured as an indifferent electrode and coupled to the first and/or second pacing electrodes 138a, 138b. The first pacing electrode 138a is disposed at a proximal end 144 of enclosure 130, and the second pacing electrode 138b is disposed at a distal end 146 of the enclosure 130, as shown in FIG. 1. The first and second pacing electrodes 138a, 138b can be configured to sense ECG signals from several vectors including the vector across a sensing electrode(s) located on the lead body 110 versus one or more of the pacing electrodes. Alternatively, in some embodiments, the ECG vector can be configured to be across one or more of the first and second pacing electrodes 138a, 138b and the enclosure 130. The first and second pacing electrodes 138a, 138b may be capable of delivering up to 10V for very short periods of time.

The cardiac lead 102 can include one or more sensing electrodes (e.g., a sensing ring electrode). As shown in FIG. 1, the cardiac lead 102 includes a sensing electrode 140 (e.g., a sensing ring electrode) that is disposed on the lead body 110 adjacent to the distal end 106. The sensing electrode 140 is an ECG electrode that is configured to detect one or more electrical signals from the heart of a patient. Thus, the sensing electrode 140 can be used to detect an abnormal electrical signal pattern (e.g., a cardiac arrhythmia).

The first and second pacing electrodes 138a, 138b and the sensing electrode 140 are typically made of one or more materials with superior corrosion resistance and/or typical of those used in the construction of implantable cardiac pacing and defibrillation leads. Example materials from which the first and second pacing electrodes 138a, 138b and the sensing electrode 140 may be made include platinum alloy materials.

The implantable medical device 100 further includes an implantable pulse generator (IPG). The IPG can be connected to the cardiac lead 102 via the first lead connector 120 and/or the second lead connector 122. The IPG can supply power to the heat exchange module 104. When an episode of atrial arrhythmia is sensed (e.g., via the sensing electrode 140) and determined to meet therapy criteria, the IPG supplies power to the heat exchange module 104. The Peltier element of the heat exchange module 104 cools a first exterior of the heat exchange module 104 to a setpoint temperature. The heat exchange module 104 further cools the cardiac tissue that is in contact with and in proximity to the heat exchange module 104. Upon completion of the cooling therapy, the ECG signal(s) is analyzed (e.g., via the sensing electrode 140) to determine the next step in the treatment.

The IPG can include one or more of the following: a power supply, a controller, a processor, an ECG sensing means, a cardiac pacing means, a temperature sensing and controlling means, a means for storing and processing feedback information obtained from the electrodes and temperature sensors. The IPG may contain a feedback control in its pulse generator circuit for temperature monitoring and control of the hot and cold surface temperatures of the Peltier device. The feedback control may provide feedback to detect scenarios where inadequate temperature dissipation is occurring (e.g., when the hot surface of the heat exchange module 104 reaches a temperature of about 45 degrees Celsius to about 55 degrees Celsius). The feedback control may provide feedback where the device temperature is below the desired minimal temperature (e.g., when the cold surface of the heat exchange module 104 reaches a temperature of about 5 degrees Celsius to about 0 degrees Celsius). The feedback control may provide feedback when the device is not reaching a therapeutic temperature (e.g., the desired cold temperature for cooling therapy delivery) (e.g., when the cold surface of the heat exchange module 104 fails to reach a temperature of about 15 degrees Celsius to about 5 degrees Celsius). The implantable medical device 100 may include a sensor to detect a change in a voltage or an impedance in the one or more temperature sensors.

The implantable medical device 100 can include several programmable parameters such as cooling temperature setpoint and duration of cooling therapy. Programmable parameters of the cooling therapy may include a cooling temperature setpoint (e.g., about 5 degrees Celsius to about 15 degrees Celsius), a duration (e.g., on time) (e.g., about 5 seconds to about 60 seconds), a therapy target cooling temperature range (e.g., a minimum and a maximum therapeutic target temperature) (e.g., about 15 degrees Celsius to about 5 degrees Celsius), a maximum (e.g., a maximum threshold) cool temperature (corresponding to the cold surface of the heat exchange module 104) (e.g., about 5 degrees Celsius to about 0 degrees Celsius), a maximum (e.g., a maximum threshold) warm temperature (corresponding to the hot surface of the heat exchange module 104) (e.g., about 45 degrees Celsius to about 55 degrees Celsius), a maximum (e.g., a maximum threshold) energy or power delivery (e.g., about 200 Joules (J) to about 500 J). Safety termination of cooling therapy (e.g., the implantable medical device 100 is turned off) may result if one of the following conditions is met: the maximum cold threshold temperature is exceeded (corresponding to the cold surface of the heat exchange module 104) (e.g., about 5 degrees Celsius to about 0 degrees Celsius), the maximum hot threshold temperature is exceeded (corresponding to the hot surface of the heat exchange module 104) (e.g., about 45 degrees Celsius to about 55 degrees Celsius), the maximum threshold energy or power delivery is exceeded (e.g., about 200 J to about 500 J).

The implantable medical device 100 can further include the capability of delivering a pacing therapy. A pacing mode can be activated to pace the atrium within a programmed time period after the detection of an atrial arrythmia episode. The pacing mode on time can be concurrent with a portion of the on time of cooling therapy mode or can extend beyond the on time for cooling therapy mode. In some embodiments, the pacing mode stays off during the cooling therapy mode. Multiple combinations of programmable pacing and cooling therapy modes are envisioned.

The implantable medical device 100 further includes a lead delivery tool designed to deploy the heat exchange module 104 onto the surface of a cardiac tissue (e.g., a pericardium). In one embodiment the delivery tool is tunneled into the pericardial space through an opening in a lower portion of the pericardial sac and is tunneled to the oblique sinus of the left atrium where the heat exchange module 104 is positioned and deployed.

Figure 2A:
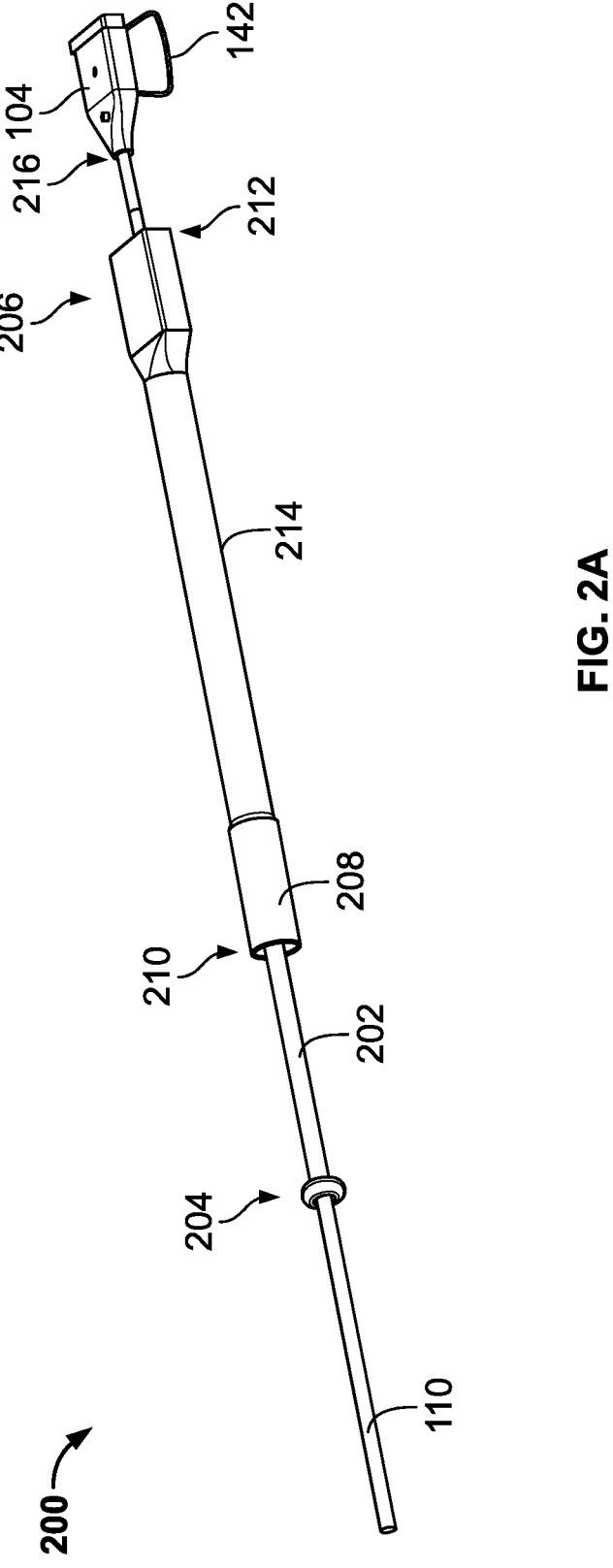
FIG. 2A is a perspective view of an example delivery tool of the implantable medical device of FIG. 1.
Figure 2B:
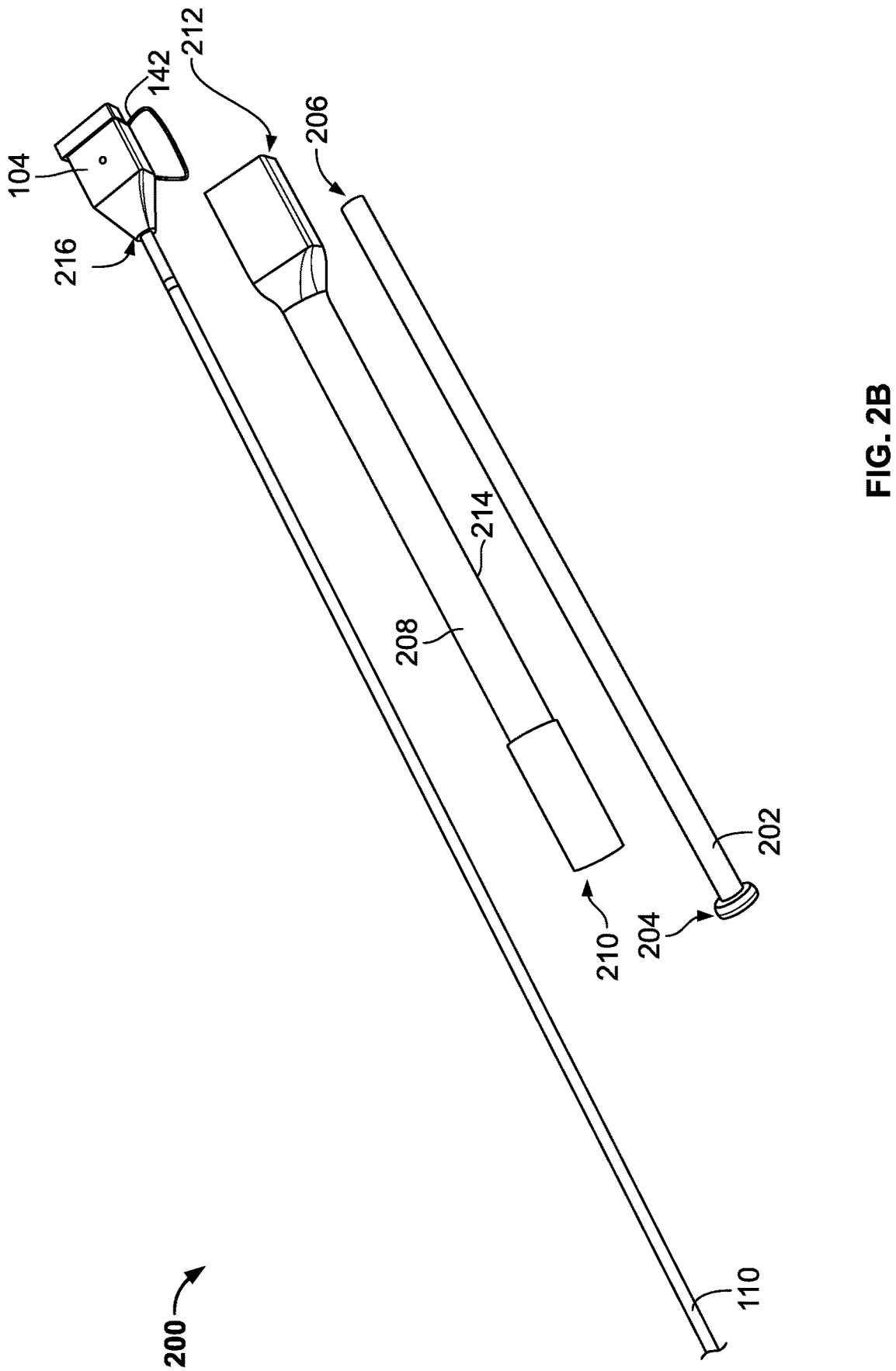
FIG. 2B is an exploded view of the example delivery tool of FIG. 2A.
Figure 3:
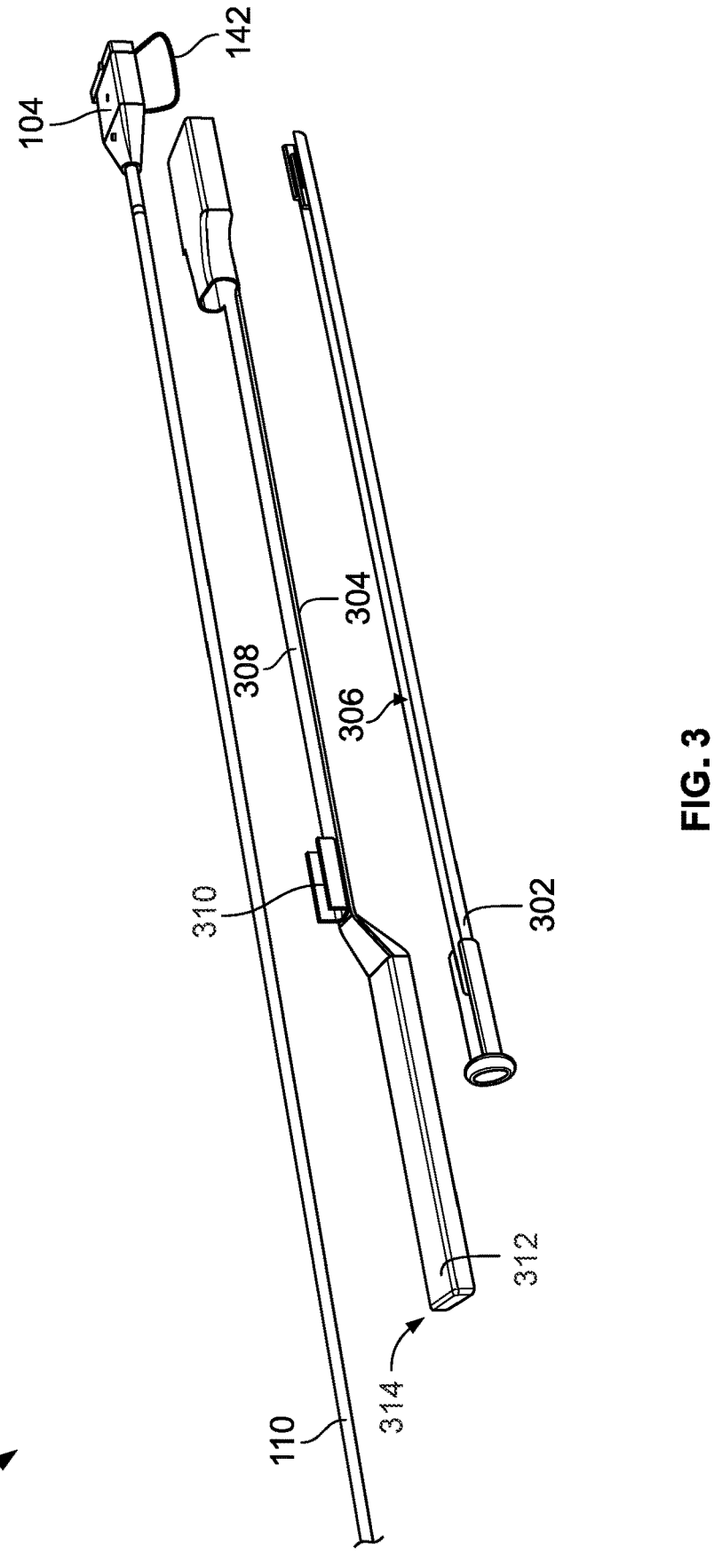
FIG. 3 is an exploded view of an example delivery tool of the implantable medical device of FIG. 1.

Two example lead delivery tools 200, 300 are shown in FIGS. 2 and 3. Both delivery tools 200, 300 can each be part of the implantable medical device 100. Referring to FIGS. 2A and 2B, the implantable medical device 100 further includes a delivery tool 200. The delivery tool 200 includes a sheath 202 having a proximal end 204 and a distal end 206. The sheath 202 defines an interior region that is sized and formed to slidably receive the lead body 110. The interior region of the sheath 202 includes a lumen extending between the proximal end 206 and the distal end 204. The lumen has a circular opening disposed at each of the proximal and distal ends 206, 204. The sheath 202 has a tubular body defining the interior region of the sheath 202. The sheath 202 is sized and formed to axially fit and slide into an axial portion of a case 208.

The tubular body of the sheath 202 typically has a length of about 14 centimeters (cm) to about 30 cm (e.g., about 16 cm). The tubular body of the sheath 202 typically has an outer diameter of about 2.5 millimeters (mm) to about 4.0 mm (e.g., about 4.5 mm). The tubular body of the sheath 202 typically has an inner diameter of about 2.0 millimeters (mm) to about 3.5 mm (e.g., about 3.0 mm). Example materials from which the sheath 202 may be made include common surgical tool materials such as, but not limited to, 304 or 316 stainless steel, or from a semi-rigid thermoplastic such as PEEK or polycarbonate.

The delivery tool 200 further includes a case 208 having a proximal end 210 and a distal end 212. The distal end 212 is formed to enclose or receive the heat exchange module 104 or a portion thereof. The distal end 212 can be generally rectangular or have a shape that is complementary to the shape of the heat exchange module 104. The distal end 212 of the case 208 is configured to secure the heat exchange module 104 while the cardiac lead 102 is being tunneled and positioned in the pericardial space. The fixation filaments 142 of the heat exchange module 104 are compressed and captured inside the distal end 212 of the case 208 when the heat exchange module 104 is loaded into the distal end 212 of the case 208. The case 208 includes a body 214 that is elongate, generally tubular, and is formed to receive the sheath 202. The body 214 extends from the proximal end 210 to the distal end 212.

The body 214 of the case 208 typically has a length of about 15 centimeters (cm) to about 28 cm (e.g., about 19 cm). The body 214 of the case 208 typically has an outer diameter of about 7.0 millimeters (mm) to about 10 mm (e.g., about 8.6 mm). The body 214 of the case 208 typically has an inner diameter of about 6.5 millimeters (mm) to about 9.5 mm (e.g., about 8.1 mm). Example materials from which the case 208 may be made include common surgical tool materials such as, but not limited to, 304 or 316 stainless steel, from a semi-rigid thermoplastic such as PEEK or polycarbonate, from a flexible or malleable material, or any combination thereof.

The sheath 202 is designed to fit against or abut the proximal portion 216 of the heat exchange module 104. In use, the sheath 202 is configured to secure the heat exchange module 104 in place while the case 208 is withdrawn. When the case 208 is withdrawn, the fixation filaments 142 of the heat exchange module 104 expand, exerting a spring tension that pushes against adjacent tissue, thereby securing the heat exchange module 104 in place within a cardiac region (e.g., the pericardial space). The sheath 202 is withdrawn once the heat exchange module 104 is secured in place by sliding the sheath 202 along the lead body 110 of the cardiac lead 102. When the sheath 202 is removed from a surgical site, the lead body 110 slides through the distal end 212 of the case 208 when the delivery tool 200 is removed.

A delivery tool may be substantially similar in construction and function in several aspects to the delivery tool 200 discussed above but can include an alternative case and sheath instead of case 208 and sheath 202. In some embodiments, the case and sheath may have an axial groove or notch. Such axial grooves or notches can provide a user (e.g., a clinician) with an alternative way to manipulate the heat exchange module 104 during implantation to achieve successful delivery and fixation to a portion of cardiac tissue (e.g., pericardial tissue).

FIG. 3 illustrates an example of a delivery tool 300 including a sheath 302 and a case 304. The sheath 302 has an open, semicylindrical body that defines an axial groove 306 sized and formed to receive the lead body 110. The case 304 includes an elongate body including a surface 308 configured to receive the sheath 302 and a retention clasp 310 configured to removably secure the sheath 302. The surface 308 is a flat surface sized to receive the body of the sheath 302. The case 304 further includes a handle 312 disposed at a proximal end 314 of the elongate body of the case 304.

In use, when the case 304 is withdrawn, the user can remove the sheath 302 from the retention clasp 310 by pulling the sheath 302 away from the retention clasp 310. Then, the fixation filaments 142 of the heat exchange module 104 expand, exerting a spring tension that pushes against adjacent tissue, thereby securing the heat exchange module 104 in place within a cardiac region (e.g., the pericardial space). The sheath 302 is withdrawn once the heat exchange module 104 is secured in place by sliding the sheath 302 along the lead body 110 of the cardiac lead 102 while the lead body 110 is slidably received in the axial groove 306.

FIG. 4 is a flowchart of a method 400 for treating a cardiac arrythmia in a patient in need thereof, in accordance with some embodiments provided herein. In some embodiments, the method 400 can be performed by, or using, the implantable medical device 100 described herein.

In step 402, a clinician (e.g., a surgeon) makes an incision into a pericardial tissue of the patient. In some embodiments, the clinician makes an incision into a fibrous pericardium, a serous pericardium, a parietal pericardium, and/or a visceral pericardium. In some embodiments, the clinician makes an incision underneath the xyphoid. In some embodiments, making the incision (e.g., step 402) further includes making an incision into an epicardial space of the patient.

In step 404, the clinician inserts the implantable medical device 100 described herein through the incision. The clinician may guide the implantable medical device 100 to a target area. For example, in some embodiments, the clinician guides the implantable medical device 100 to an oblique sinus of the heart. Delivering the implantable medical device 100 to the oblique sinus of the heart can advantageously provide a secure location where movement of the implantable medical device 100 is minimized. Additionally, delivering the implantable medical device 100 to the oblique sinus of the heart can advantageously target a cardiac tissue of interest for the treatment of the cardiac arrythmia.

In step 406, the clinician secures the heat exchange module 104 of the implantable medical device 100 to a surface of a cardiac tissue using one of the delivery tools 200, 300 described herein. For example, the clinician withdraws the case 208 of delivery tool 200 while maintaining sheath 202 in place and abutting case 208 to the proximal portion 216 of the heat exchange module 104. In some embodiments, the clinician exerts a pushing force against the proximal portion 216 of the heat exchange module 104 to ensure the heat exchange module 104 remains in place while the fixation filaments 142 deploy. In some embodiments, the step of securing the heat exchange module (e.g., step 406) further includes attaching a suture sleeve 134 of the implantable medical device 100 to the cardiac tissue. In some embodiments, the suture sleeve is removably coupled and/or slidably coupled to the lead body 110.

In step 408, a surface of the secured heat exchange module 104 is cooled to a therapeutic temperature for a therapeutic period of time. In some embodiments, the therapeutic temperature ranges from about 5 degrees Celsius to about 15 degrees Celsius In some embodiments, the therapeutic period of time ranges from about 5 seconds (s) to about 60 s (In some embodiments, the surface that is cooled contacts the target tissue (e.g., a pericardial tissue such as, but not limited to, a visceral layer of a serous pericardial tissue that may include an epicardial tissue) prior to cooling. In some embodiments, as a first surface is cooled, a second surface of the heat exchange module 104 gradually warms up. In some embodiments, the second surface is configured to contact a cardiac tissue opposite of the target tissue (e.g., a pericardial tissue such as, but not limited to, a parietal layer of a serous pericardial tissue and/or a fibrous pericardial tissue) when the implantable medical device 100 is implanted.

In some embodiments, the methods described herein can further include detecting a cardiac arrhythmia by using the one or more sensing electrodes 140 disposed on the lead body 110 of the cardiac lead 102. In some embodiments, the one or more sensing electrodes 140 detect a cardiac arrythmia prior to initiating the cooling therapy (e.g., cooling a first surface of the heat exchange module 104). In some embodiments, the one or more sensing electrodes 140 detect a cardiac arrythmia after initiating the cooling therapy (e.g., cooling a first surface of the heat exchange module 104). In some embodiments, the methods described can further include cooling the first surface of the implantable medical device upon detection of the cardiac arrhythmia. For example, in some embodiments, ECG detection of a cardiac arrhythmia can trigger the initiation of the cooling therapy (e.g., cooling of the first surface of the heat exchange module 104). The cooling therapy may be applied for a prescribed period of time or in conjunction with continuous arrhythmia monitoring until the arrhythmia is terminated.

While the above-discussed implantable medical device 100 has been described and illustrated with respect to certain dimensions, shapes, arrangements, configurations, material formulations, and methods, in some embodiments, an implantable medical device that is otherwise substantially similar in construction and function to the implantable medical device 100 may include one or more dimensions, shapes, arrangements, configurations, and/or materials formulations that are different from the ones discussed above or may be used with respect to methods that are modified as compared to the methods described above. For example, while the implantable medical device 100 has been described and illustrated as including a cardiac lead 102 including a bifurcation 114 where the lead body 110 splits into a first portion 116 of the lead body 110 and a second portion 118 of the lead body 110, in some embodiments, a cardiac lead that is otherwise substantially similar in construction and function to the cardiac lead 102 may alternatively include a division point where the lead body splits into one or more portions of the lead body. In some embodiments, the lead body may split into 1, 2, 3, 4, 5, or more portions of the lead body.

While the implantable medical device 100 has been described and illustrated as including bifurcation 114 that can be positioned at a location that is about 75% distal from the distal end 106 of the cardiac lead 102, in some embodiments, the bifurcation 114 can be positioned at a location that is about 15 to about 30% distal from the distal end 106 of the cardiac lead 102. In some embodiments, the bifurcation 114 can be positioned at any location along the lead body 110 between the distal end 106 and the proximal end 108 of the cardiac lead 102.

While the implantable medical device 100 has been described and illustrated as including a first and second lead connectors 120, 122, in some embodiments, the implantable medical device 100 includes one or more lead connectors. In some embodiments, the implantable medical device 100 includes at least about 1 to about 5 (e.g. about 1 to 2, about 2 to 3, about 3 to 4, about 4 to 5) lead connectors. In some embodiments, the first lead connector 120 is a DF4 connector. In some embodiments, the first lead connector 120 is an IS4 connector. In some embodiments, the first lead connector 120 is an IS1 connector. In some embodiments, the first lead connector 120 is a lead connector that is different than a DF4, IS4, and/or IS1 connector. In some embodiments, the first lead connector 120 is connectable to a commercially available implantable cardiac device (e.g., an implantable cardioverter defibrillator (ICD), an implantable pulse generator (IPG), or the like). In some embodiments, the first lead connector 120 is a custom connector that is different than a DF4, IS4, and/or IS1 connector. In some embodiments, the second lead connector 122 is also a custom connector that is different than a DF4, IS4, and/or IS1 connector. In some embodiments, these are connectable to a commercially available implantable cardiac device (e.g., an ICD, an IPG, or the like).

While the implantable medical device 100 has been described and illustrated as including a first and second lead connectors 120, 122, in some embodiments, the implantable medical device 100 includes a single lead connector. In some embodiments, the single lead connector includes one or more connector or lead terminal rings. For example, in some embodiments, the single lead connector includes about 1 to about 10 lead terminal rings (e.g., about 1 to 2, 2 to 3, 3 to 4, 4 to 5, 5 to 6, 6 to 7, 7 to 8, 8 to 9, or 9 to 10 lead terminal rings). In some embodiments, any one of the lead terminal rings of the single lead connector can be configured to be or to connect to one or more conductors (e.g., a common/return conductor, one or more temperature sensors, a sensing electrode, a reference sensing electrode, a pacing conductor, a reference sensing electrode, or the like). In some embodiments, having a single lead connector results in having no bifurcation in the lead body.

While the implantable medical device 100 has been described and illustrated as including six lead terminal rings 128*a*, 128*b*, 128*c*, 128*d*, 128*e*, 128*f*, in some embodiments, the first and second lead connectors 120, 122 each include one or more lead terminal rings. In some embodiments, the first and second lead connectors 120, 122 each include about 1 to about 10 lead terminal rings (e.g., about 1 to 2, 2 to 3, 3 to 4, 4 to 5, 5 to 6, 6 to 7, 7 to 8, 8 to 9, or 9 to 10 lead terminal rings).

While the implantable medical device 100 has been described and illustrated as including an enclosure 130 of the heat exchange module 104 that is substantially rectangular, in some embodiments, it should be understood that other form factors are also envisioned. For example, in some embodiments, enclosure 130 has contoured surfaces rather than planar surfaces. In some such embodiments, enclosure 130 can be specifically contoured to interface with a particular anatomy of a patient.

While the implantable medical device 100 has been described and illustrated as delivering cooling therapy to a cardiac tissue, in some embodiments, the implantable medical device 100 may have the ability to also deliver anti-tachycardia pacing therapy to terminate certain arrhythmias. In some embodiments, the implantable medical device 100 may not have the ability to also deliver anti-tachycardia pacing therapy to terminate certain arrhythmias.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment.

Conversely, various features that are described in the context of a single embodiment can also be implemented in multiple embodiments separately or in any suitable sub-combination. Moreover, although features may be described herein as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures do not necessarily require the particular order shown, or sequential order, to achieve desirable results. In certain implementations, multitasking and parallel processing may be advantageous.

What is claimed is:

1. An implantable medical device comprising:
a cardiac lead sized for insertion in a cardiac cavity, the cardiac lead having a distal end and a proximal end and a lead body extending therebetween;
a heat exchange module disposed at the distal end of the lead body, the heat exchange module comprising an enclosure having a first surface and a second surface;
one or more temperature sensors located within the enclosure; and
a delivery tool system comprising:
a sheath comprising a proximal end, a distal end, and an elongate body extending therebetween, the sheath defining a region configured to slidably receive the lead body, the distal end of the sheath configured to exert a pushing force against the heat exchange module; and
a case comprising: (i) a distal end that is shaped generally rectangular in correspondence to the heat exchange module and that is sized for releasably enclosing the heat exchange module and (ii) an elongate body defining a lumen or a surface configured to slidably receive the sheath.

2. The implantable medical device of claim 1, further comprising one or more pacing electrodes disposed at the distal end of the lead body.

3. The implantable medical device of claim 2, wherein the one or more pacing electrodes are disposed at a proximal and/or a distal end of the heat exchange module.

4. The implantable medical device of claim 1, further comprising one or more sensing electrodes disposed on the lead body.

5. The implantable medical device of claim 1, wherein the elongate body of the case comprises a retention clasp configured to removably secure the sheath.

6. The implantable medical device of claim 1, wherein the case comprises a handle at a proximal end of the elongate body, and wherein the sheath and case are composed of a flexible or malleable material.

7. The implantable medical device of claim 1, further comprising a suture sleeve disposed between the distal end and the proximal end of the cardiac lead, the suture sleeve configured to secure the implantable medical device adjacent to a cardiac tissue.

8. The implantable medical device of claim 7, wherein the suture sleeve is removably coupled and/or slidably coupled to the lead body.

9. The implantable medical device of claim 1, further comprising one or more connectors at the proximal end of the cardiac lead, the one or more connectors configured to connect to a power supply.

10. The implantable medical device of claim 9, wherein the one or more connectors comprise one or more lead terminal pins and one or more lead terminal rings.

11. The implantable medical device of claim 9, wherein the power supply is an implantable cardiac device.

12. The implantable medical device of claim 11, wherein the implantable cardiac device is an implantable cardioverter defibrillator (ICD), a pacemaker, or an external pulse generator.

13. The implantable medical device of claim 1, wherein the first surface of the heat exchange module is configured to be set to a first temperature that is less than a second temperature of the second surface of the heat exchange module.

14. The implantable medical device of claim 13, wherein the first temperature ranges from about 1 degree Celsius to about 37 degrees Celsius, and the second temperature ranges from about 37 degrees Celsius to about 50 degrees Celsius.

15. The implantable medical device of claim 1, wherein the heat exchange module comprises a heat pump located within the enclosure, and a heat sink located within the enclosure, the heat sink including a phase change material and a thermally conductive interface structure positioned between the heat pump and the phase change material, wherein the heat exchange module is configured to be an indifferent electrode.

16. The implantable medical device of claim 1, wherein the heat exchange module comprises one or more fixation filaments configured to secure the heat exchange module adjacent to a cardiac tissue, the one or more fixation filaments being loop-shaped and biased in an outward direction.

17. A method of treating a cardiac arrythmia in a patient in need thereof, the method comprising:

making an incision into a pericardial tissue of the patient;

inserting, using a delivery tool system, an implantable medical device through the incision, the implantable medical device comprising:

a cardiac lead sized for insertion in a cardiac cavity, the cardiac lead having a distal end and a proximal end and a lead body extending therebetween;

a heat exchange module disposed at the distal end of the lead body, the heat exchange module comprising an enclosure having a first surface and a second surface; and one or more temperature sensors located within the enclosure;

securing the heat exchange module to a surface of a cardiac tissue, wherein the delivery tool system comprises:

a sheath having a proximal end, a distal end, and an elongate body extending therebetween, the sheath defining a region configured to slidably receive the lead body, the distal end of the sheath configured to exert a pushing force against the heat exchange module; and a case having: (i) a distal end that is shaped generally rectangular in correspondence to the heat exchange module and that is sized for releasably enclosing the heat exchange module and (ii) an elongate body defining a lumen or a surface configured to slidably receive the sheath; and cooling the first surface of the implantable medical device to a therapeutic temperature for a therapeutic period of time.

* * * * *